United States Patent [19]

Peake et al.

[11] Patent Number: 4,603,147

[45] Date of Patent: Jul. 29, 1986

[54] BIOCIDAL FLUOROALKANES AND FLUOROALKENES

[75] Inventors: Clinton J. Peake, Trenton, N.J.; John F. Engel, Washington Crossing, Pa.

[73] Assignee: FMC Corporation, Philadelphia, Pa.

[21] Appl. No.: 675,111

[22] Filed: Nov. 27, 1984

Related U.S. Application Data

[63] Continuation-in-part of Ser. No. 559,143, Dec. 7, 1983, abandoned.

[51] Int. Cl.$^4$ .................. A01N 29/02; A01N 29/00
[52] U.S. Cl. ................................. 514/743; 514/761; 514/744
[58] Field of Search ............... 514/744, 757, 761, 746, 514/743

[56] References Cited

U.S. PATENT DOCUMENTS

| | | | |
|---|---|---|---|
| 2,785,984 | 3/1957 | Kenaga | 99/153 |
| 2,904,601 | 9/1959 | Ilgenfritz | 260/653 |
| 2,904,602 | 9/1959 | Ilgenfritz | 260/653.3 |
| 2,904,603 | 9/1959 | Ilgenfritz | 260/653 |
| 3,255,076 | 6/1966 | Weil et al. | 514/758 |
| 3,655,786 | 4/1972 | Gilbert et al. | 260/653.3 |

FOREIGN PATENT DOCUMENTS

| | | | |
|---|---|---|---|
| 3244641 | 12/1981 | Fed. Rep. of Germany | 54/744 |
| 42-21494 | 10/1967 | Japan | 514/744 |
| 56-83406 | 7/1981 | Japan | 514/741 |
| 56-127301 | 10/1981 | Japan . | |
| 56-128701 | 10/1981 | Japan | 514/746 |
| 56-169602 | 12/1981 | Japan . | |

OTHER PUBLICATIONS

Chemical Abstracts, vol. 48, (1954); #1407b, Ruh.
Chemical Abstracts, vol. 49, (1955); #4702c, Ruh.
Chemical Abstracts, vol. 51, (1957); #664d, Ruh.
Burton & Kehoe, "The Copper(I)Chloride-Ethanolamine Catalyzed Addition of Polyfluorinated Alkanes to Olefins", Tetrahedron Letters, No. 42, pp. 5163-5168, 1966.
Davies, Haszeldine, Rowland & Tipping, "Fluoro-Olefin Chemistry, Part 16, Reaction of Hexafluoropropine with n-Butane and n-Propane", J. Chem. Soc., Perkin Trans I, pp. 109-114, 1983.
Burton et al., Tetrahedron Letters 42: 5163-5168, (1966).

Primary Examiner—Leonard Schenkman
Assistant Examiner—Joseph A. Lipovsky
Attorney, Agent, or Firm—Harrison H. Young, Jr.; H. Robinson Ertelt

[57] ABSTRACT

A method is described for the control of nematodes and soil-borne insects in agricultural crops which comprises applying to the situs of infestation a composition containing as active ingredient a compound of the formula $$R-Z-(CH_2)_n-Q$$

wherein R is an alkyl radical of one or two carbon atoms carrying one-to-four fluorine substituents and one-to-three chlorine or bromine substituents represented as $CF_pX_{(3-p)}-$ or $CF_rX_{(3-r)}-CF_sX_{(2-s)}-$; Z is $-(CH_2-CHX)-$ or $-(CH=CH)-$; X is chlorine or bromine; Q is methyl, isopropyl, tert-butyl, or $C_3-C_6$ cycloalkyl; n is 5 to 12 as required to yield in the compound a chain of 10 to 16 carbon atoms; p is 1 or 2; r is 2 or 3; s is 0 or 1 or 2. A process for preparation of active ingredient compounds is described, and utility of compositions against nematodes and soil-borne insects is exemplified.

6 Claims, No Drawings

BIOCIDAL FLUOROALKANES AND FLUOROALKENES

This present application is a continuation-in-part of U.S. Ser. No. 559,143 filed Dec. 7, 1983 now abandoned.

This invention relates to chemical compounds which are useful as active ingredients in compositions for controlling nematodes and soil-borne insects in agricultural crops. More particularly, the invention relates to the use as a nematicide and insecticide of chlorofluoro- and bromofluoroalkanes and -alkenes comprising 10 to 20 carbon atoms in which one or more of the carbons is perhalogenated.

The patent literature discloses lower ($C_3$–$C_5$) alkanes and alkenes carrying fluorine, chlorine, and bromine substituents, alone or in combination, for which utility as insecticides and nematicides is disclosed, most often as fumigants. No reference has been found which discloses nematicidal or insecticidal activity for the compounds of the present invention.

Chemical compounds useful as active ingredients in the compositions of the present invention may be represented by the structure:

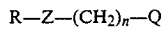

wherein
R is an alkyl radical of one or two carbon atoms carrying one-to-four fluorine substituents and one-to-three chlorine or bromine substituents, represented as $CF_pX_{(3-p)}$— or $CF_rX_{(3-r)}$—$CF_sX_{(2-s)}$;
Z is —($CH_2$—CHX)— or —(CH=CH)—;
X is chlorine or bromine;
Q is methyl, isopropyl, tert-butyl, or $C_3$–$C_6$ cycloalkyl;
n is 5 to 12 with the proviso that the total length of the carbon chain shall be not less than ten carbon atoms and not greater than sixteen carbon atoms;
p is 1 or 2;
r is 2 or 3;
s is 0 or 1 or 2.

Active ingredients in which Z is —(CH=CH)— may comprise mixtures of position isomers, geometric isomers, and optical isomers. In the position isomers, R—Z— may be represented as
$CY_3$—CH=CH— and $CY_2$=CH—CHY—, or
$CY_3CY_2$—CH=CH— and $CY_3CY$=CH—CHY—,
in which Y is fluorine, chlorine, or bromine.

Geometric isomers will occur when hydrogens are on the same side of the double bond (cis), or on opposite sides of the double bond (trans) in the —CH=CH— structure. Optical isomers can occur each time an asymmetric carbon is present, as in the —CHY— group, or —$CY_2$— group when the Y's differ; asymmetric carbons and hence optical isomers may be found in the saturated compounds as well as in their dehydrohalogenated analogs.

Unless a contrary intent is expressed, the invention embodies and includes the individual optical and geometric and position isomers, and combinations or mixtures thereof.

Preferred active ingredients are those in which Q is methyl, and R is selected from $CX_2F$—, $CXF_2$—, $CXF_2CX_2$—, $CF_3CX_2$—, $CXF_2CXF$—, and $CXF_2CF_2$—.

Especially preferred active ingredients are those in which RZ is selected from $CClF_2CH_2$—CHBr—, $CClF_2CH$=CH—, $CBrF_2CH_2$—CHBr—, $CBrF_2CH$=CH—, $CClF_2CClFCH_2$—CHCl—, $CClF_2CClFCH$=CH—, $CBrF_2CF_2CH_2$—CHBr—, $CBrF_2CF_2CH$=CH—, and in which the carbon chain contains an even number of carbon atoms, for example $C_{10}$, $C_{12}$, and $C_{14}$.

The biocidal chlorofluoro- and bromofluoroalkanes of this invention were prepared utilizing the method described by Burton and Kehoe, Tetrahedron Letters, 42, 5163–68(1966) in which a 1-octene is caused to react with a one-, two-, or three-carbon fluorohaloalkane in the presence of cuprous chloride and ethanolamine in tert-butanol. Corresponding alkenes were obtained by dehydrohalogenation of the previously obtained long-chain fluorohaloalkanes with 1,8-diazabicyclo[5.4.0]undec-7-ene in diethyl ether or with no solvent.

Alkenes useful in the first reaction described above include straight-chain 1-alkenes of seven to fifteen carbon atoms. It is contemplated that straight-chain alpha, omega-dienes of similar length may be used, resulting in perhalo radicals at both ends of the chain. Straight-chain alkenes in which the double bond occurs at a position remote from the terminal position, for example in the 2-, 3-, or 5-position, may be utilized to obtain fluorohaloalkanes with branching from the carbon chain, ordinarily a mixture of position isomers.

Fluorohaloalkanes useful in the process for preparing the compounds of the invention include, but are not limited to, $CCl_3F$, $CClBrF_2$, $CBr_2F_2$, $CClF_2CCl_3$, $CF_3CCl_3$, $CF_3CBr_3$, $CF_3CCl_2F$, $CF_3CClF_2$, $CCl_2FCCl_2F$, $CClF_2CCl_2F$, $CBrF_2CBrF_2$. It is contemplated that three-carbon fluoroalkanes may also be used in the process.

Preparation of the active ingredients is described in the following examples. In the descriptions which follow, all temperatures are in degrees Celsius, and reduced pressures are in mm Hg (1 mm Hg=133.3 Pascals).

EXAMPLE 1

1,2,4-TRICHLORO-1,1,2-TRIFLUORODODECANE

Into a pressure bottle was placed 15.1 ml (0.08 mole) of 1-decene, 19.2 ml (0.16 mole) of 1,1,2-trichloro-1,2,2-trifluoroethane, 0.07 g (0.0007 mole) of copper(I)chloride, 2.4 ml (0.04 mole) of ethanolamine and 70 ml of tert-butanol. The bottle was flushed with dry argon and closed, and the mixture was stirred at 90° C. for 64 hours. The reaction mixture was cooled to room temperature, filtered and the solvent evaporated from the filtrate under reduced pressure to leave an oily residue. The residue was dissolved in pentane, and the solution was washed in succession with three portions of water and one portion of a saturated aqueous sodium chloride solution. The pentane solution was dried over anhydrous sodium sulfate, the sodium sulfate was removed by filtration, and the solvent was evaporated from the filtrate under reduced pressure to give a green liquid. The green liquid was purified by distillation under reduced pressure to yield 11.35 g of 1,2,4-trichloro-1,1,2-trifluorododecane; by 70°–72°/0.025 mm Hg. The nmr spectrum was consistent with the assigned structure.

Analysis calc'd for $C_{12}H_{20}Cl_3F_3$: C 43.99; H 6.15; Found: C 44.47; H 6.21.

The compound of Example 1 is listed in Table 1 as Compound 3. Other compounds prepared by this process, or a slight modification thereof, were 1,2,4,5, 9–13, 17–20, 24–28, 32–35, 39–42, 44, 45, and 48. The nmr spectra of these compounds were consistent with the assigned structures, and analyses for carbon and hydrogen were consistent with expected values.

EXAMPLE 2

1,2-DICHLORO-1,1,2-TRIFLUORODODEC-3-ENE

A solution of 0.91 ml (0.0061 mole) of 1,8-diazabicyclo[5.4.0]undec-7-ene in 10 ml of methylene chloride was added dropwise to a stirred solution of 2.0 g (0.0061 mole) of 1,2,4-trichloro-1,1,2-trifluorododecane (Product of Example 1) in 20 ml of methylene chloride. The resultant mixture was stirred at room temperature for 24 hours, then heated at reflux for 48 hours. There being no evidence that any reaction had occurred, the reaction mixture was cooled to room temperature, the solvent distilled from the mixture and 30 ml of dry diethyl ether added to the residue. The resultant mixture was stirred at room temperature for five hours, then washed with three portions of water. The washed organic solution was dried over anhydrous sodium sulfate and filtered to remove the sodium sulfate; the filtrate was heated under reduced pressure to yield an oily residue. The residue was purified by distillation under reduced pressure to yield 0.77 g of product designated as 1,2-dichloro-1,1,2-trifluorododec-3-ene; bp 72°–74°/0.65 mm Hg. The nmr spectrum was consistent with the assigned structure.

Analysis calc'd for $C_{12}H_{19}Cl_2F_3$: C 49.50; H 6.58; Found: C 49.20; H 6.46.

The compound prepared in Example 2 is listed in Table 1 as Compound 6. Compounds 7, 8, 14–16, 21–23, 29–31, 36–38, 43, 46, 47, and 49 were also prepared in a similar manner, using diethyl ether as the solvent. The nmr spectra and elemental analyses for carbon and hydrogen were consistent with assigned structure.

BIOLOGICAL TESTING

The compounds of Examples 1–49 were formulated and tested for nematicidal activity as formulated materials. The formulation used was a standard 5 weight percent dust formulation made up as follows:
Test compound: 5 parts
Base: 95 parts
  96%-attapulgite clay
  2%-highly purified sodium lignosulfonate (100%)
  2%-powdered sodium alkylnaphthalenesulfonate (75%);
the mixture was ground to a fine powder.

ROOT-KNOT NEMATODE

The formulations described above were tested for activity against root-knot nematode (*Meloidogyne incognita*) as follows:

Namatode Culture—Tomato seedlings with two large true leaves were transplanted into 15.2-cm clay pots containing steam-sterilized sandy soil. One week after transplanting, galled roots of nematode-infected tomato plants, with fully developed egg masses, were placed in three holes in the soil around the seedling roots. Holes were then closed with soil. The plants were allowed to grow until fully developed egg masses were formed (6 to 7 weeks after inoculation).

Inoculum Preparation—Infected tomato roots, containing egg masses, were cleaned under running tap water, cut into short pieces and comminuted with water in an electrical blender for 30 seconds. The shredded roots were poured onto layers of washed sand in a wooden flat. The flat was covered with plastic sheeting and kept at greenhouse temperatures for 3 to 7 days to allow about 50% of the larvae to hatch.

Preparation of Root-Knot Nematode Infested Soil—Samples of the infested soil prepared as described above were processed for nematodes by using the Caveness and Jensen centrifugal-sugar flotation extraction technique [Caveness, F. E. and Jensen, H. J., "Modification of the Centrifugal Flotation Technique for the Isolation and Concentration of Nematodes and their Eggs from Soil and Plant Tissue", Proc. Helm. Soc., Washington, 22, 87–89 (1955)].

Fine wire cloth screen (No. 500, U.S.A. Standard Sieve Series) was used to collect the nematodes and eggs, and their number was estimated under a stereomicroscope. Sand containing 4000 to 5000 eggs and larvae was mixed in a Twin Shell Blender with sufficient additional steam-sterilized sandy soil to provide 2000 g infested soil.

Fumigation of Infested Soil—The formulated compound to be tested for nematicidal activity was incorporated in the infested soil and mixed further in the Twin Shell Blender, and the lot was placed in a glass jar and sealed for three days. The treatment rate was 25 ppm (weight test compound/weight of soil) or lower.

Nematicidal Evaluation—The fumigated infested soil was divided among four 10.2-cm fiber pots, approximately 500 g/pot. A young tomato plant or cucumber plant was planted in each pot. Young tomato or cucumber plants were also planted in 10.2-cm fiber pots containing 500 g infested soil which had not been treated with a test compound. Both sets of pots were placed in the greenhouse and received the same culturing.

At the end of two weeks the roots of all plants were examined and rated in comparison to untreated checks, using the following system:

KNOT INDEX

4 No control—amount of swellings equivalent to that developed on the roots of the untreated check plants.
3 Amount of swellings 25% less than that developed on the roots of the untreated check plants.
2 Amount of swellings 50% less than that developed on the roots of the untreated check plants.
1 Amount of swellings 75% less than that developed on the roots of the untreated check plants.
0 No swellings—complete control.

When the control observed is between 1 and 0 the Knot Index is subdivided to indicate how close the control is to 75% or to 100%. For this subdivision numbers between 0 and 1 are used as follows:
0.8: 80% control
0.5: 90% control
0.4–0.1: 95–99% control The knot index for the untreated check was 4.0. Results for the compositions of the invention are recorded as percent control in Table 1.

STUNT, CYST, AND LESION NEMATODE

Evaluation of compositions of the invention against stunt nematode (*Tylenchorhynchus claytoni*) was carried out by incorporating the formulated active ingredient in soil in which a corn seedling was then planted, and two days thereafter inoculating the soil with stunt nematode in mixed stages of growth, from larvae to adults. The soil was processed for nematode counting approximately five weeks after treatment. Untreated check plants showed no nematode control. Compound No. 3 showed 40% control of stunt at 15 ppm active ingredient and 23% control at 5 ppm.

Compositions were also evaluated against cyst nematode (*Heterodera schachtii*), following a similar procedure in which soybean seedlings were planted instead of corn seedlings. Untreated check plants showed no control of cyst nematode. Compound No. 3 at 10 ppm active ingredient showed 50% and 88% control of cyst in separate tests, each consisting of the average of four replicates.

Compositions were also evaluated against lesion nematode (*Pratylenchus penetrans*), following a similar procedure in which pea seedlings were planted instead of corn seedlings, and nematodes were extracted from the root systems, instead of from the soil. Untreated plants showed no nematode control. Compound No. 3 showed 4% control at 15 ppm active ingredient.

SOIL INSECTICIDE EVALUATION

Compounds 1, 4, 6, 26, 29, 31, 32, 37, and 49 were evaluated for initial activity against larvae of southern corn rootworm (*Diabrotica undecimpunctata howardi*) using the method of G. R. Sutter, J. Econ. Entomol 75, 489-91 (1982) with minor modifications. In this method candidate compounds are tested at successively lower concentrations in duplicate, along with two untreated checks: Two three-day-old corn sprouts and ten early third-stage (9- to 10-day-old) larvae were placed in a three-ounce plastic cup containing 30 g of clay loam soil and a measured quantity of test compound, mixed together 30 minutes beforehand; the cups were covered with a plastic lid and held in a closed plastic bag during incubation at 74°-78° F. for 48 hours, at which time mortality to larvae was determined. Results of these evaluations of initial activity, recorded in Table 2, indicate that Compounds 1, 6, 26, 29, 31, and 49 are 100% effective against rootworm larvae at 4 ppm, and Compounds 1, 6, 26, 31, and 49 are 80% effective or better at 1 ppm. Residual activity of active ingredients against rootworm larvae was determined in the same manner except that treated soil was not infested with larvae until 7 days after treatment. Corn sprouts were placed in each cup and mixed with treated soil immediately before larvae were placed in the soil. In this test at 4 ppm, Compounds 26 and 49 retained 95% and 90%, respectively, of the activity observed in the test for initial activity.

The biocidal compositions of this invention are those in which the active ingredient is present in admixture with an agriculturally acceptable carrier, diluent, or extender.

The nematicides and insecticides of this invention, like most agricultural chemicals, are generally not applied full strength, but are formulated with agriculturally acceptable carriers normally employed for facilitating the dispersion of active ingredients, various additives, and optionally with other active ingredients, recognizing the accepted fact that the formulation and mode of application of a toxicant may affect the activity of the material. The present compounds may be applied, for example, to the soil in which nematode or soil insect control is desired as granules or powders or liquids, the choice of application varying, of course, with the nematode or soil insect species and environmental factors present at the particular locus of infestation. Thus, the compounds may be formulated as granules of various sizes, as dusts, as wettable powders, as emulsifiable concentrates, as solutions, as dispersions, as controlled release compositions, and the like.

A typical formulation may vary widely in concentration of the active ingredient depending on the particular agent used, the additives and carriers used, other active ingredients, and the desired mode of application. With due consideration of these factors, the active ingredients of a typical formulation may, for example, be suitably present at a concentration of from about 0.5% up to about 99.5% by weight of the formulation. Substantially inactive ingredients such as adjuvants and carriers may comprise from about 99.5% by weight to as low as about 0.5% by weight of the formulation. Surface active agents, if employed in the formulation, may be present at various concentrations, suitably in the range of 1 to 30% by weight. Provided below is a general description of exemplary types of formulations which may be employed for dispersion of the biocides of the present invention.

Dusts are admixtures of the active ingredient with finely divided solid carriers and/or diluents such as talc, natural clays, kieselguhr, pyrophyllite, chalk, diatomaceous earths, calcium phosphates, calcium and magnesium carbonates, sulfur, lime, flours, and other organic and inorganic solid carriers. These finely divided formulations generally have an average particle size of less than about 45 μm, (No. 325, U.S.A. Standard Sieve Series). In most cases, the active ingredient will be present in dust formulations at a concentration in the range of 1 to 15%, and occasionally from 1% to about 30%, the balance of the composition typically being agriculturally acceptable carrier or diluent.

Wettable powders, also useful formulations for these biocides, are in the form of finely divided particles which disperse readily in water or other liquid vehicles. The wettable powder is ultimately applied to the soil or plant as a dry dust or a dispersion in water or other liquid. Typical carriers for wettable powders include fuller's earth, kaolin clays, silicas, and other highly absorbent or adsorbent inorganic diluents. The concentration of active ingredient in wettable powders is dependent upon physical properties of the active ingredient and the absorbency characteristics of the carrier. Liquids and low melting solids (mp <100° C.) are suitably formulated in the concentration range of 5 to 50% by weight, usually from 10 to 30%; high melting solids (mp >100° C.) are formulated in the range of 5 to 95% by weight, usually 50 to 85%. An agriculturally acceptable carrier or diluent, frequently including a small amount of a surfactant to facilitate wetting, dispersion, and suspension, accounts for the balance of the formulation.

Granules are admixtures of the active ingredients with solids of particle sizes generally in the range of 4.75 mm to 150 μm (No. 4 to No. 100, U.S.A. Standard Sieve Series). Granular formulations may employ hard core materials such as sands and other silicates, mineral carbonates, sulfates or phosphates and the like, or porous cores such as attapulgite clays, fuller's earth, kieselguhr, chalk, diatomaceous earths, ground corn cobs, wood dusts and the like. Impregnating or binding agents such as aliphatic and aromatic petroleum solvents, alcohols, ethers, ketones, esters, vegetable oils, polyvinyl acetates, polyvinyl alcohols, dextrins, sugars and the like are commonly used to aid in coating or impregnating the solid carriers with the active ingredient. Emulsifying agents, wetting agents, dispersing agents, and other additives known in the art may also be added.

A typical granular formulation may suitably contain from about 1% to about 50% by weight active ingredient and 99% to 50% by weight of inert materials.

Microencapsulated or other controlled release formulations may also be used with biocides of this invention for control of nematodes and soil insects.

Emulsifiable concentrates (EC's) are homogeneous liquid compositions, usually containing the active ingredient dissolved in a liquid carrier. Commonly used liquid carriers include xylene, heavy aromatic naphthas, isophorone, and other nonvolatile or slightly volatile organic solvents. For application of the active ingredient, these concentrates are dispersed in water, or other liquid vehicle, forming an emulsion, and are normally applied as a spray to the area to be treated. The concentration of the essential active ingredient in EC's may vary according to the manner in which the composition is to be applied, but, in general, is in the range of 0.5 to 95%, frequently 10 to 80%, by weight of active ingredient, with the remaining 99.5 to 5% being surfactant and liquid carrier.

Flowables are similar to EC's except that the active ingredient is suspended in a liquid carrier, generally water. Flowables, like EC's, may include a small amount of a surfactant, and contain active ingredient in the range of 0.5 to 95%, frequently from 10 to 50%, by weight of the composition. For application, flowables may be diluted in water or other liquid vehicle, and are normally applied as a spray to the area to be treated.

Typical wetting, dispersing or emulsifying agents used in nematicidal formulations include, but are not limited to, the alkyl and alkylaryl sulfonates and sulfates and their sodium salts; alkylamide sulfonates, including fatty methyl taurides; alkylaryl polyether alcohols, sulfated higher alcohols; polyethylene oxides; sulfonated animal and vegetable oils; sulfonated petroleum oils; fatty acid esters of polyhydric alcohols and the ethylene oxide addition products of such esters; and the addition product of long-chain mercaptans and ethylene oxide. Many other types of useful surface-active agents are available in commerce. The surface-active agent, when used, normally comprises from 1 to 15% by weight of the biocidal composition.

Other useful formulations include simple solutions of the active ingredient in a relatively non-volatile solvent such as corn oil, kerosene, propylene glycol, or other organic solvents. This type of formulation is particularly useful for ultra low volume application.

The concentration of the biocide in use dilution is normally in the range of about 2% to about 0.1%. Many variations of spraying, dusting, soil-incorporated, and controlled or slow release compositions in the art may be used by substituting or adding a compound of this invention into compositions known or apparent to the art.

Compositions of the present invention may be formulated and applied with other suitable active ingredients, including nematicides, insecticides, acaricides, fungicides, plant regulators, herbicides, fertilizers, or with synergists.

In applying the foregoing chemicals, whether alone or with other agricultural chemicals, an effective biocidal amount must be applied. While the application rate will vary widely depending on the choice of compound, the formulation and mode of application, the plant species being protected and the planting density, a suitable use rate may be in the range of 0.5 to 25 kg/hectare, preferably 1 to about 20 kg/hectare. Trees and vines for example may require at least 5 kg/hectare whereas annuals such as corn may require considerably lower rates of application, for example 1 to 5 kg/hectare.

Various modifications may be made in the formulation and application of the novel compositions of this invention without departing from the inventive concept herein, as defined in the claims below.

TABLE 1

Fluorinated Haloalkanes and Haloalkenes:
Root Knot Nematode Control at 25 ppm
Active Ingredient as Soil Fumigant

| Cpd. No. | Compound bp °C./m m Hg | Percent Control |
|---|---|---|
| 1 | $CClF_2-CClF-CH_2-CHCl-(CH_2)_5-CH_3$<br>45–47°/0.03 m m | 100 |
| 2 | $CClF_2-CClF-CH_2-CHCl-(CH_2)_6-CH_3$<br>50–53°/0.025 m m | 25 |
| 3 | $CClF_2-CClF-CH_2-CHCl-(CH_2)_7-CH_3$<br>70–72°/0.025 m m | 100 |
| 4 | $CClF_2-CClF-CH_2-CHCl-(CH_2)_8-CH_3$<br>84–94°/0.35–0.45 m m | 97* |
| 5 | $CClF_2-CClF-CH_2-CHCl-(CH_2)_9-CH_3$<br>90–100°/0.75 m m | 99* |
| 6 | $CClF_2-CClF-CH=CH-(CH_2)_7-CH_3$<br>72–74°/0.65 m m | 100 |
| 7 | $CClF_2-CClF-CH=CH-(CH_2)_8-CH_3$<br>80–82°/0.45 m m | 17 |
| 8 | $CClF_2-CClF-CH=CH-(CH_2)_9-CH_3$<br>85–87°/0.55 m m | 75 |
| 9 | $CF_3-CCl_2-CH_2-CHCl-(CH_2)_5-CH_3$<br>81–81.5°/7.0 m m | 6 |
| 10 | $CF_3-CCl_2-CH_2-CHCl-(CH_2)_6-CH_3$<br>95–95.5°/7.0 m m | 50 |
| 11 | $CF_3-CCl_2-CH_2-CHCl-(CH_2)_7-CH_3$<br>112—115°/8.0 m m | 38 |
| 12 | $CF_3-CCl_2-CH_2-CHCl-(CH_2)_8-CH_3$<br>118°/7.0 m m | 100 |
| 13 | $CF_3-CCl_2-CH_2-CHCl-(CH_2)_9-CH_3$<br>132°/7.0 m m | 50 |
| 14 | $CF_3-CCl_2-CH=CH-(CH_2)_7-CH_3$<br>65–66.5°/0.40 m m | 50 |
| 15 | $CF_3-CCl_2-CH=CH-(CH_2)_8-CH_3$<br>79–80°/0.40 m m | 25 |
| 16 | $CF_3-CCl_2-CH=CH-(CH_2)_9-CH_3$<br>100°/4.5 m m | 38 |
| 17 | $CCl_2F-CH_2-CHCl-(CH_2)_6-CH_3$<br>70.5–72.5°/0.45 m m | 25 |
| 18 | $CCl_2F-CH_2-CHCl-(CH_2)_7-CH_3$<br>92–93°/0.75 m m | 0 |
| 19 | $CCl_2F-CH_2-CHCl-(CH_2)_8-CH_3$<br>90–96°/0.40 m m | 31 |
| 20 | $CCl_2F-CH_2-CHCl-(CH_2)_9-CH_3$<br>110–115°/0.60 m m | 0 |
| 21 | $CCl_2F-CH=CH-(CH_2)_7-CH_3$<br>124°/16 m m | 86 |
| 22 | $CCl_2F-CH=CH-(CH_2)_8-CH_3$<br>129°/12 m m | 98 |
| 23 | $CCl_2F-CH=CH-(CH_2)_9-CH_3$<br>96–99°/0.75 m m | 86 |
| 24 | $CBrF_2-CH_2-CHBr-(CH_2)_6-CH_3$<br>76–77°/135 m m | 98 |
| 25 | $CBrF_2-CH_2-CHBr-(CH_2)_7-CH_3$<br>151–152°/23 m m | 12 |
| 26 | $CBrF_2-CH_2-CHBr-(CH_2)_8-CH_3$<br>104–106°/0.65 m m | 100 |
| 27 | $CBrF_2-CH_2-CHBr-(CH_2)_9-CH_3$<br>113–115°/0.65 m m | 0 |
| 28 | $CBrF_2-CH_2-CHBr-(CH_2)_{10}-CH_3$<br>119–120°/0.65 m m | 95 |
| 29 | $CBrF_2-CH=CH-(CH_2)_8-CH_3$<br>70–75°/0.5 m m | 97 |
| 30 | $CBrF_2-CH=CH-(CH_2)_9-CH_3$<br>85°/0.5 m m | 50 |
| 31 | $CBrF_2-CH=CH-(CH_2)_{10}-CH_3$<br>95–102°/0.45 m m | 98 |
| 32 | $CBrF_2-CF_2-CH_2-CHBr-(CH_2)_5-CH_3$<br>76–80°/0.55 m m | 78 |

TABLE 1-continued

Fluorinated Haloalkanes and Haloalkenes:
Root Knot Nematode Control at 25 ppm
Active Ingredient as Soil Fumigant

| Cpd. No. | Compound bp °C./m m Hg | Percent Control |
|---|---|---|
| 33 | $CBrF_2-CF_2-CH_2-CHBr-(CH_2)_6-CH_3$ 87–90°/0.9 m m | 38 |
| 34 | $CBrF_2-CF_2-CH_2-CHBr-(CH_2)_7-CH_3$ 100°/0.5 m m | 79 |
| 35 | $CBrF_2-CF_2-CH_2-CHBr-(CH_2)_8-CH_3$ 110–111°/0.95 m m | 0** |
| 36 | $CBrF_2-CF_2-CH=CH-(CH_2)_5-CH_3$ 48°/0.5 m m | 44 |
| 37 | $CBrF_2-CF_2-CH=CH-(CH_2)_7-CH_3$ 82°/0.4 m m | 95 |
| 38 | $CBrF_2-CF_2-CH=CH-(CH_2)_8-CH_3$ 99°/0.8 m m | 17** |
| 39 | $CClF_2-CCl_2-CH_2-CHCl-(CH_2)_5-CH_3$ 90°/0.65 m m | 17 |
| 40 | $CClF_2-CCl_2-CH_2-CHCl-(CH_2)_6-CH_3$ 100–101°/0.8 m m | 79 |
| 41 | $CClF_2-CCl_2-CH_2-CHCl-(CH_2)_7-CH_3$ 105–107°/0.60 m m | 69 |
| 42 | $CClF_2-CCl_2-CH_2-CHCl-(CH_2)_8-CH_3$ 119–121°/0.75° | 0** |
| 43 | $CClF_2-CCl_2-CH=CH-(CH_2)_8-CH_3$ 106°/0.55° | 0** |
| 44 | $CCl_2F-CClF-CH_2-CHCl-(CH_2)_5-CH_3$ 86°/0.45 m m | 17 |
| 45 | $CCl_2F-CClF-CH_2-CHCl-(CH_2)_7-CH_3$ 110.5–112°/0.70 m m | 13 |
| 46 | $CCl_2F-CClF-CH=CH-(CH_2)_8-CH_3$ 112°/0.85 m m | 0** |
| 47 | $CBrF_2-CF_2-CH=CH-(CH_2)_9CH_3$ 90–91°/0.6 m m | 83** |
| 48 | $CClF_2-CH_2-CHBr-(CH_2)_8-CH_3$ 69.5°/0.15 m m | 100** |
| 49 | $CClF_2-CH=CH-(CH_2)_8-CH_3$ 90–91°/5.8 m m | 100** |

*Soil incorporated at 25 ppm without fumigation.
**Active ingredient at 10 ppm as soil fumigant.

TABLE 2

Control of Southern Corn Rootworm by
Fluorinated Haloalkanes and Haloalkenes

| Compound No. | Rate (ppm) | Initial % Kill* |
|---|---|---|
| 1 | 4.0 | 100 |
|  | 2.0 | 100 |
|  | 1.0 | 80 |
| 4 | 4.0 | 65 |
|  | 2.0 | 55 |
|  | 1.0 | 55 |
| 6 | 4.0 | 100 |
|  | 2.0 | 90 |
|  | 1.0 | 85 |
| 26 | 4.0 | 100 |

TABLE 2-continued

Control of Southern Corn Rootworm by
Fluorinated Haloalkanes and Haloalkenes

| Compound No. | Rate (ppm) | Initial % Kill* |
|---|---|---|
|  | 2.0 | 100 |
|  | 1.0 | 95 |
| 29 | 4.0 | 100 |
|  | 2.0 | 80 |
|  | 1.0 | 25 |
| 31 | 4.0 | 100 |
|  | 2.0 | 90 |
|  | 1.0 | 85 |
| 32 | 4.0 | 80 |
|  | 2.0 | 20 |
|  | 1.0 | 5 |
| 37 | 4.0 | 85 |
|  | 2.0 | 15 |
|  | 1.0 | 10 |
| 49 | 4.0 | 100 |
|  | 2.0 | 95 |
|  | 1.0 | 80 |

*Two days after first contact of larvae and active ingredient.

We claim:

1. A method for the control of root-knot and cyst nematodes or soil-borne insects of the genus Diabrotica by applying to the soil at the situs of infestation a nematicidally or insecticidally effective amount of a composition containing as active ingredient a compound selected from the group consisting of $CClF_2-CClF-CH_2-CHCl-(CH_2)_5-CH_3$,
$CClF_2-CClF-CH_2-CHCl-(CH_2)_7-CH_3$,
$CClF_2-CClF-CH_2-CHCl-(CH_2)_8-CH_3$,
$CClF_2-CClF-CH_2-CHCl-(CH_2)_9-CH_3$,
$CF_3-CCl_2-CH_2-CHCl-(CH_2)_8-CH_3$,
$CClF_2-CClF-CH=CH-(CH_2)_7-CH_3$,
$CCl_2F-CH=CH-(CH_2)_8-CH_3$,
$CBrF_2-CH_2-CHBr-(CH_2)_6-CH_3$,
$CBrF_2-CH_2-CHBr-(CH_2)_8-CH_3$,
$CBrF_2-CH_2-CHBr-(CH_2)_{10}-CH_3$,
$CBrF_2-CH=CH-(CH_2)_8-CH_3$,
$CBrF_2-CH=CH-(CH_2)_{10}-CH_3$,
$CBrF_2-CF_2-CH_2-CHBr-(CH_2)_7-CH_3$,
$CBrF_2-CF_2-CH=CH-(CH_2)_7-CH_3$,
$CBrF_2-CF_2-CH=CH-(CH_2)_9-CH_3$,
$CClF_2-CH_2-CHBr-(CH_2)_8-CH_3$, and
$CClF_2-CH=CH-(CH_2)_8-CH_3$.

2. The method of claim 1 for the control of root-knot and cyst nematodes.

3. The method of claim 1 for the control of *Meloidogyne incognita*.

4. The method of claim 1 for the control of *Heteroderas schachtii*.

5. The method of claim 1 for the control of soil-borne insects of the genus Diabrotica.

6. The method of claim 1 for the control of *Diabrotica undecimpunctata howardi*.

* * * * *